US007422608B2

United States Patent
Molenda et al.

(10) Patent No.: US 7,422,608 B2
(45) Date of Patent: Sep. 9, 2008

(54) COLOR ENHANCING SHAMPOO COMPOSITION

(75) Inventors: Michael Molenda, Frankfurt (DE); Frank Golinski, Ober-Ramstadt (DE)

(73) Assignee: KPSS-KAO Professional Salon Services GmbH, Darmstadt (DE)

( * ) Notice: Subject to any disclaimer, the term of this patent is extended or adjusted under 35 U.S.C. 154(b) by 311 days.

(21) Appl. No.: 11/268,343

(22) Filed: Nov. 7, 2005

(65) Prior Publication Data

US 2006/0100114 A1    May 11, 2006

(30) Foreign Application Priority Data

Nov. 9, 2004    (EP)    ............................ 04026522

(51) Int. Cl.
*A61Q 5/10* (2006.01)
(52) U.S. Cl. ............... 8/405; 8/406; 8/435; 8/552; 8/554; 8/644; 8/654
(58) Field of Classification Search ............. 8/405, 8/406, 435, 552, 554, 644, 654
See application file for complete search history.

(56) References Cited

U.S. PATENT DOCUMENTS

| 7,135,045 B2* | 11/2006 | Carrascal et al. ............... 8/405 |
| 2001/0042276 A1* | 11/2001 | Kawasoe et al. ............... 8/405 |
| 2004/0087668 A1 | 5/2004 | Schmucker-Castner et al. .. 516/90 |
| 2004/0180030 A1* | 9/2004 | Maubru .................... 424/70.21 |
| 2005/0226838 A1* | 10/2005 | Krause et al. ............ 424/70.13 |

FOREIGN PATENT DOCUMENTS

| EP | 1 366 754 A1 | 12/2003 |
| EP | 1 428 497 A1 | 6/2004 |
| WO | WO 03/086335 A1 | 10/2003 |
| WO | WO 2004/054526 A1 | 7/2004 |

* cited by examiner

*Primary Examiner*—Eisa B Elhilo

(57) ABSTRACT

The present invention concerns a shampoo composition with color enhancing effect and showing optimum hair conditioning properties, especially shine, softness and good manageability. Composition comprises at least one cleansing and lathering surfactant, at least one cationic hair dye and at least one hydroxycarboxylic acid and/or dicarboxylic acid.

15 Claims, No Drawings

COLOR ENHANCING SHAMPOO COMPOSITION

FIELD OF THE INVENTION

The present invention concerns a shampoo composition with color enhancing effect and showing optimum hair conditioning properties, especially shine, softness and good manageability.

BACKGROUND OF THE INVENTION

Color enhancing and cleansing compositions have been known for years and have proven to be very successful on the market.

Such shampoo compositions customarily comprise hair coloring direct dyestuffs together with the at least one surface-active substance, in particular an anionic surfactant, and a hair-conditioning polymer, preferably of the cationic type.

Although these products are proven as such to be satisfying consumer needs, it is still desirable to improve their efficiency especially in terms of hair shine, softness and manageability together with good colour enhancing ability, and certainly with other hair conditioning properties in particular with regard to volume and body, and combability.

SUMMARY OF THE INVENTION

Thus, the object of the present invention is providing a cleansing composition showing excellent colour enhancing and cleansing abilities together with excellent shine enhancing effect, improving excellently manageability and softness of hair, at the same time having optimum conditioning effects on hair, which satisfies consumer expectations in terms of combability, volume and body, and nice feeling on touching hair.

It has surprisingly been found out that a shampoo composition comprising at least one cleansing and lathering surfactant, at least one cationic hair dye and at least one hydroxycarboxylic acid and/or dicarboxylic acid, show optimum performance in colour enhancing and especially surprisingly excellently superior performance in hair shine improving, excellently improving hair manageability and softness of hair. The compositions of the present invention improve also combability, volume and body of hair. After washing hair with the compositions of present invention, hair feels nicer when touching. The effects mentioned are more pronounced on repeated usage.

EP 1174112 discloses hair cosmetic compositions comprising organic acid, organic solvent, cationic surfactant and higher alcohol and having pH in the range of 2 to 6 for improving hair shine. Additionally, WO 2004/047777 discloses leave-in compositions for hair comprising malic and lactic acids and organic solvents for improving shine, setting and touch feeling. Both documents are silent on color enhancing and cleansing compositions comprising cationic direct dyes.

The pH of the compositions according to the present invention is suitably below 4.5 and preferably in the range of 2.5 to 4.0, more preferably 2.9 to 3.8.

The pH of the compositions is adjusted with hydroxycarboxilic acids and/or dicarboxylic acids. In those cases where selected hydroxycarboxylic acid and/or dicarboxylic acid concentration is not enough to reach the selected pH, other organic and inorganic acids can as well be used to adjust pH to the required value. The hydroxycarboxilic acids useful in the compositions of the present invention are lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid.

DETAILED DISCRIPTION OF THE INVENTION

Compositions according to invention in principal comprise at least one hydroxycarboxilic acid and/or dicarboxylic acid. Combinations of two or more hydroxycarboxylic acids and/or dicarboxylic acids are also within the scope of the invention. It should be noted that hydroxycarboxylic acid and dicarboxylic acid comprising compositions are also within the scope of the present invention. Especially preferred hydroxyliccarboxylic acids are the lactic and malic acids. Malic acid is also a discarboxy acid. The most preferred hydroxycarboxylic acid and/or dicarboxylic acid is the malic acid.

Total hydroxycarboxylic acid and/or dicarboxylic acid concentration in the composition of the present invention varies in the range form 0.1 to 5% by weight, preferably 0.25 to 3% by weight, more preferably 0.5 to 3% by weight and most preferably 0.75 to 3% by weight. In a preferred embodiment of the invention, the compositions of the present invention comprise at least 0.5% malic acid.

According to the invention, colour enhancing cleansing composition comprises at least one direct acting cationic dyestuff. Suitable cationic dyestuffs are in principal those available on the market for hair colouring applications. Some examples to those are:

Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14 and Basic Yellow 57.

For this purpose, special reference is made to the PCT application WO 95/15144 of Ciba-Geigy AG. The cationic dyestuffs with the following chemical structures are especially preferred ones according to the present invention.

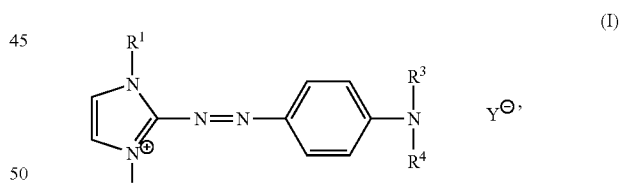

(I)

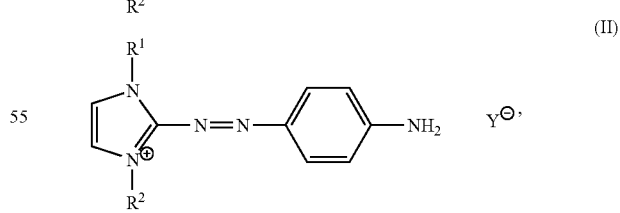

(II)

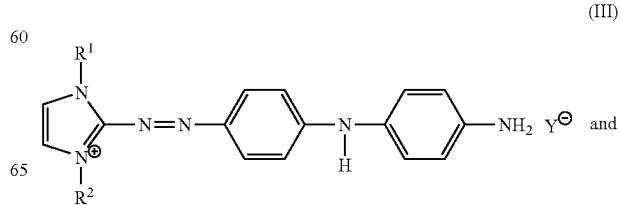

(III)

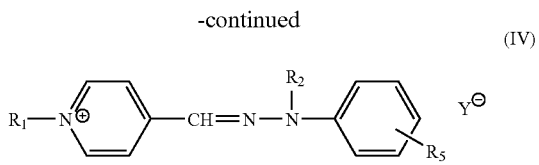

wherein $R^1$, $R^2$, $R^3$ and $R^4$ stand for hydrogen, a $CH_3$— or $C_2H_5$— group, $R^5$ stands for hydrogen, —$OCH_3$ or —$OC_2H_5$ and Y is an anion such as chloride, bromide, methosulfate.

The most preferred cationic dyestuffs are the ones according to the formula I, where $R_1$, $R_2$, $R_3$ and $R_4$ are methyl and Y is chloride, according to formula II where $R_1$ and $R_2$ are methyl and Y is chloride and according to the formula IV, where $R_1$ and $R_2$, are methyl, $R_5$ is hydrogen and Y is methosulfate.

Cationic dyestuffs are included into the compositions of the present invention at a concentration of 0.0001 to 2%, preferably 0.0001 to 1.5% and more preferably 0.0001 to 1% by weight, calculated to total aqueous composition.

Anionic dyes may as well be used in combination with cationic direct dyes at minor quantities. The suitable ones are:

Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

According to the invention, anionic dyes may be included in minor quantities at a concentration around 25%, preferably not more than 10% of the total cationic dye content of the composition.

Additionally, the coloring compositions of the present invention may comprise neutral dyes (HC dyes), so called nitro dyes in addition to the cationic direct dyes. Concentration of those can typically be in the range of 0.0001 to 1%, preferably 0.0001 to 0.75% and more preferably 0.0001 to 0.5% by weight calculated to total aqueous composition.

Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs may also be used in combination with cationic direct-acting dyestuffs, for example henna (red or black), alkanna root, laccaic acid, indigo, logwood powder, madder root and rhubarb powder, etc.

The anionic, HC and plant dyes are always used in combination with cationic direct dyes.

Hair cleansing colour enhancing compositions of the present invention can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbondioxide, dimethylether and alkanes such as butane propane or their mixtures.

Cleansing colour enhancing compositions of the present invention comprise at least one surfactant selected from anionic, non-ionic and/or amphoteric or zwitterionic surfactants at a concentration range of 1 to 50%, preferably 5 to 40% and more preferably 5 to 30%, and most preferably 5 to 25% by weight, calculated to the total composition.

In an embodiment of the present invention cleansing colouring enhancing composition of the present invention, comprises at least one anionic, at least one nonionic surfactant. More preferably the compositions further comprise additionally at least one amphoteric surfactant.

Anionic surfactants suitable within the scope of the invention are preferably present in an amount from 1 to about 30%, preferably 2 to 20% and most preferably 2-15%, and most preferably 2 to 10% by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride(ether)sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

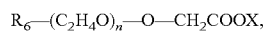

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

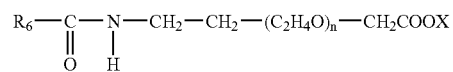

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof. It is also possible to use mixtures of several anionic surfactants, for example an ether sulfate and a polyether carboxylic acid or alkyl amidoether carboxylic acid.

An overview of the anionic surfactants used in liquid body cleansing compositions can furthermore be found in the monography of K. Schrader, "Grundlagen und Rezepturen der Kosmetika", $2^{nd}$ Ed. (1989, Huthig Buchverlag), pp. 595-600 and pp. 683 to 691.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Further surfactants in the shampoo compositions according to the invention are nonionic surfactants in admixture with anionic surfactants.

These are described in Schrader, l.c., on pages 600-601 and pp. 694-695. Especially suited are alkyl polyglucosides of the general formula

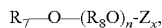

$$R_7—O—(R_8O)_n-Z_x,$$

wherein $R_7$ is an alkyl group with 8 to 18 carbon atoms, $R_8$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides which may be present in an amount from 0.25% to 5% by weight, calculated to the total composition.

Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl)amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

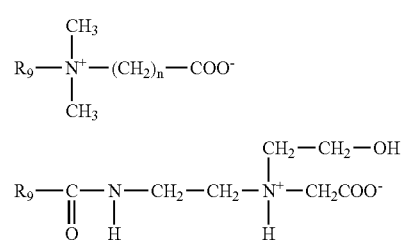

wherein $R_9$ is a $C_8$-$C_{18}$-alkyl group and n is 1 to 3; sulfobetaines of the structure

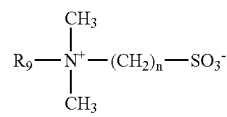

wherein $R_9$ and n are same as above;
and amidoalkyl betaines of the structure

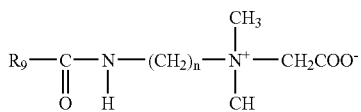

wherein $R_9$ and n are same as above.

The composition of the present invention comprises hair-conditioning agents. Conditioning agents can be selected from oily substances, non-ionic substances, cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula

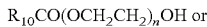

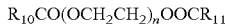

where $R_{10}$ and $R_{11}$ are independent from each other saturated, unsaturated or branched or non-branched alkyl chain with 7 to 21 C atoms and n is typically 2-100.

In one of the preferred from of the present invention, coloring enhancing cleansing compositions comprise at least one cationic polymer as conditioning agent. Suitable cationic polymers are those of best known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

It has further been found out that especially those of cationic cellulose type polymers known as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, polyquaternium 6 and polyquaternium 7.

The cationic polymers also include the quaternized products of graft polymers from organopolysiloxanes and polyethyl oxazolines described in EP-A 524 612 and EP-A 640 643.

Colour enhancing cleansing compositions of the present invention can comprise additionally one or more cationic surfactant(s) as conditioner presented with the general formula

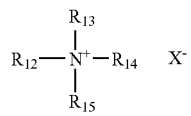

where $R_{12}$ is a saturated or unsaturated, branched or non-branched alkyl chain with 8-22 C atoms or

where $R_{16}$ is saturated or unsaturated, branched or non-branched alkyl chain with 7-21 C atoms and n has value of 1-4, or

where $R_{17}$ is saturated or unsaturated, branched or non-branched alkyl chain with 7-21 C atoms and n has value of 1-4, and $R_{13}$ is hydrogen or unsaturated or saturated, branched or non-branched alkyl chain with 1-4 C atoms or

or

where $R_{16}$, $R_{17}$ and n are same as above.

$R_{14}$ and $R_{15}$ are hydrogen or lower alkyl chain with 1 to 4 carbon atoms, and X is anion such as chloride, bromide, methosulfate.

Typical examples of those ingredients are cetyl trimethly ammonium chloride, stear trimonium chloride, behentrimoinium chloride, stearamidopropyl trimonuim chloride, dioleoylethyl dimethyl ammonium methosulfate, dioleoylethyl hydroxyethylmonium methosulfate.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, silicon oil and derivatives and cationic surfactants can be 0.01-5% by weight, preferably 0.01-3.5% by weight, more preferably 0.05-2.5% and most preferably 0.1-1.5% by weight calculated to the total composition.

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water-or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskole® VAP 343", vinyl pyrrolidone/(meth)acrylic acid ester copolymers, as well as chitosan derivatives.

Amphoteric polymers are found to be useful in conditioning shampoo composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl meth-acrylates of the type "Yukaformer®", e.g., the butyl methacrylate copolymer "Yukaformer® Am75"; copolymers from monomers containing carboxyl groups and sulfonic groups, e.g., (meth)acrylic acid and itaconic acid, with monomers such as mono- or dialkyl amino alkyl(meth)acrylates or mono- or dialkyl-aminoalkyl(meth)acrylamides containing basic groups, in particular amino groups; copolymers from N-octyl acrylamide, methyl methacrylate, hydroxypropyl methacrylate, N-tert.-butyl aminoethyl methacrylate and acrylic acid, as well as the copolymers known from U.S. Pat. No. 3,927,199, are applicable.

Cleansing color enhancing composition of the present invention can be transparent as well as pearly. Transparency of the composition is judged by naked eye in a transparent shampoo bottle with a thickness not more than 5 cm. In the case a transparent appearance is wished, the following ingredients are not essential. However, pearl-shiny appearance is achieved with those dispersed in cleansing color enhancing compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kind of mixtures is available commercially.

In another preferred form of the invention, It has been found out that in the presence of organic solvents the effects especially the shine enhancing effect of the compositions is very much enhanced. Without being bound by any theory, it is thought that the accelerated/more pronounced effect is observed due to penetration enhancing effect of the organic solvents. Accordingly, colour enhancing cleansing composition can comprise organic solvents such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzyloxyethanol and polypropylene glycols. Concentration of organic solvents in the shampoo composition should not exceed 5% by weight, preferably in the range of 0.1 to 3%, more preferably 0.5 to 2.5% by weight calculated to total composition.

Solubilizers may be added to the compositions especially when oily substances are chosen as conditioning agents and fragrance oils with highly lipophilic properties. Typical solubilizers may be hydrogenated castor oil known with the trade mark Cremophor RH series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The coloring shampoo composition may contain active ingredients selected from UV filters, moisturisers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The UV filters are those oil and water soluble ones for the purpose of protecting hair colour. In other words, anionic and nonionic, oily, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy- benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof and/or 3-(4'-methyl benzylidene)-DL-campher. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc.

Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", $4^{th}$ Ed.

The viscosity of the conditioning shampoo compositions according to the invention is in the range of 500 and about 20,000 mPa·s at 20° C., preferably 1,000 to 10,000, in particular 1,000 to 7,000 mPa·s at 20° C., measured with Brookfield or Hoppler viscosimeters at a shear rate of 10 sec$^{-1}$. Viscosity of shampoo compositions can be adjusted with known viscosity enhancers. The preferred ones are PEG-55 propyleneglycol oleate and PEG-18 glyceryl oleate/cocoate known with the trade names Antil® 141 and 171, respectively and PEG-160 sorbitan triisostearate known with a trade name Rheodol®. It should be noted that in the case that a composition are delivered in the form of a foam from a pump-foamer and/or aerosol can, those compositions should not be thickened and have a viscosity value not more than 500 mPa·s, more preferably 250 mPa·s measured as mentioned above at room temperature.

It is self-understood that the shampoos according to the invention may comprise other substances customarily used in such compositions such as preservatives, fragrances. A list of such additives can also be found in Schrader, I.c., on pp. 695 to 722.

It should especially be noted that the effects of the inventive compositions become more and more visible after repeated usage. Especially shine enhancing effect is very much pronounced after repeated usage.

The following examples are to illustrate the invention, but not to limit. The products according to the invention are prepared by mixing the individual components in water, whereby it is also possible to use pre-mixtures of various ingredients.

EXAMPLE 1

| Sodium lauryl ether carboxylate (10EO) | 5.0 (% by wt.) |
|---|---|
| C$_8$—C$_{22}$-Alkyl glucoside (P.D.: ~1.5) | 5.0 |
| Cocoamidopropyl betaine | 5.0 |
| Cetyl PEG/PPG-10/1 dimethicone | 0.5 |
| Cationic polymer (Polyquaternium-7) | 0.1 |
| Sodium benzoate | 0.6 |
| Sodium sorbate | 0.3 |
| Benzyloxyethanol | 0.5 |
| Peach oil | 0.1 |
| Perfume | 0.7 |
| PEG-60-hydrogenated castor oil | 0.5 |
| PEG-18 Glyceryl cocoate/oleate | 1.0 |
| Basic red 76 | 0.09 |
| Basic red 51 | 0.06 |
| Malic acid | 0.75 |
| Water | ad100.0 |

The pH of the composition is 3.5. The color direction is red.

The above shampoo composition of the present invention was tested in a comparative test with 20 volunteers aging 20 to 45 years old against an identical composition (composition 1A) with a pH adjusted to 5.8 with sodium hydroxide. In addition, the same composition having the same pH was produced with using equal amount of lactic acid instead of malic acid (composition 1B), which is as well according to present invention. The compositions 1A and 1B were as well tested with 20 female volunteers. The volunteers were asked to evaluate the used shampoo composition using a questionnaire by giving marks from 1 (not good at all) to 5 (excellent). From the individual results the arithmetical average values were calculated. The evaluation was done immediately after the first usage and after 5 and 10 applications. The test period was 2 weeks being the shortest and 4 weeks being the longest.

The results are presented in the table below.

| | After 1 application Composition | | | After 5 applications Composition | | | After 10 applications Composition | | |
|---|---|---|---|---|---|---|---|---|---|
| | 1* | 1A** | 1B* | 1* | 1A** | 1B* | 1* | 1A** | 1B* |
| Wet hair | | | | | | | | | |
| Combing | 3.9 | 3.8 | 3.8 | 3.8 | 3.8 | 3.8 | 4.0 | 3.8 | 3.8 |
| Softness | 4.2 | 3.7 | 3.9 | 4.3 | 3.7 | 3.9 | 4.4 | 3.7 | 3.9 |
| Nice feel | 4.0 | 3.9 | 4.0 | 4.4 | 3.9 | 4.0 | 4.4 | 3.9 | 4.0 |
| Dry hair | | | | | | | | | |
| Combing | 3.9 | 3.6 | 3.8 | 4.0 | 3.6 | 3.8 | 4.0 | 3.6 | 3.8 |
| Softness | 3.9 | 3.7 | 3.8 | 4.2 | 3.6 | 4.0 | 4.4 | 3.7 | 4.1 |
| Nice feel | 4.1 | 3.8 | 3.9 | 4.4 | 3.8 | 4.1 | 4.3 | 3.8 | 4.0 |
| Volume | 4.2 | 3.7 | 4.0 | 4.2 | 3.7 | 4.1 | 4.3 | 3.6 | 4.1 |
| Shine | 4.4 | 3.4 | 4.2 | 4.5 | 3.3 | 4.3 | 4.7 | 3.4 | 4.5 |
| Body | 4.3 | 3.6 | 4.1 | 4.3 | 3.6 | 4.1 | 4.4 | 3.5 | 4.3 |
| Managability | 4.3 | 3.7 | 4.3 | 4.6 | 3.4 | 4.4 | 4.6 | 3.7 | 4.4 |
| Want to buy | 4.2 | 3.5 | 4.1 | 4.4 | 3.4 | 4.2 | 4.6 | 3.6 | 4.3 |

*Compositions 1 and 1B are according to the invention
**Composition 1A is not part of the invention - comparative composition From the results in the table above, it is clear that the inventive compositions 1 and 1B showed superior performance over the comparative composition 1A. The superior performance of the inventive compositions after repeated applications (5 and 10) was more pronounced. In addition, the composition 1 comprising malic acid and having pH 3.5 was superior to both lactic acid comprising composition and to the comparative composition. Lactic acid comprising composition 1B (pH 3.5—inventive) showed better performance than comparative composition.

Similar results were observed with the examples below.

EXAMPLE 2

| C$_{12}$—C$_{14}$-alkyl glucoside (P.D.: ~1.4) | 8.0 |
|---|---|
| Cocoamidopropyl betaine | 10.0 |
| Cetyl PEG/PPG-10/1 dimethicone | 0.7 |
| Cationic polymer (Polyquaternium-11) | 0.2 |
| PEG-3 distearate | 0.8 |
| Benzyloxyethanol | 0.25 |
| Perfume | 0.6 |
| Sodium benzoate | 0.6 |
| PEG-18 Glyceryl cocoate/oleate | 1.0 |
| Basic red 76 | 0.05 |
| Basic brown 16 | 0.15 |
| Basic blue 99 | 0.04 |
| Malic acid | 0.50 |
| Lactic acid | 0.50 |
| Water | ad 100.0 |

The pH of the composition is 3.3. A shampoo with very good lathering capability and hair conditioning properties especially shine enhancing effect as well as with excellent color enhancing ability was obtained. The color direction is brown.

EXAMPLE 3

| Sodium lauryl ether carboxylate (10EO) | 2.0 (% by wt.) |
|---|---|
| Disodium lauryl ether sulfosuccinate | 3.5 |

-continued

| | |
|---|---|
| Decylglucoside (P.D.: ~1.4) | 5.5 |
| Cocoamidopropyl betaine | 8.0 |
| Cetyl PEG/PPG-10/1 dimethicone | 0.5 |
| Cationic polymer (Polyquaternium-10) | 0.2 |
| Benzyloxyethanol | 0.75 |
| Sodium benzoate | 0.6 |
| Basic yellow 57 | 0.004 |
| Basic brown 16 | 0.001 |
| PEG-160 sorbitan triisostearate | 1.0 |
| Malic acid | 1.0 |
| Perfume | 0.5 |
| Water | ad 100.0 | pH of the composition is 3.4.

The properties of this shampoo corresponded with those according to Examples 1 and 2. The color observed on hair after washing and drying is warm gold.

EXAMPLE 4

| | |
|---|---|
| Sodium lauryl ether carboxylate (10EO) | 2.0 (% by wt.) |
| Disodium lauryl ether sulfosuccinate | 3.5 |
| Decylglucoside (P.D.: ~1.4) | 5.5 |
| Cocoamidopropyl betaine | 8.0 |
| Cetyl PEG/PPG-10/1 dimethicone | 0.5 |
| Cationic polymer (Polyquaternium-10) | 0.2 |
| PPG-9 | 1.0 |
| Sodium benzoate | 0.6 |
| Basic blue 99 | 0.0001 |
| Basic violet 2 | 0.000045 |
| PEG-160 sorbitan triisostearate | 0.5 |
| PEG-18 Glyceryl cocoate/oleate | 0.8 |
| Malic acid | 0.5 |
| Lactic acid | 0.25 |
| Perfume | 0.5 |
| Water | ad 100.0 |

The pH of the composition is 3.6.

The properties of this shampoo corresponded with those according to Examples 1, 2 and 3. The color observed on hair after washing and drying is shiny silver. It was also observed that the shampoo is excellently suitable for its anti-yellow effect especially on bleached hair.

EXAMPLE 5

| | |
|---|---|
| Sodium lauryl ether carboxylate (10EO) | 2.5 (% by wt.) |
| Disodium lauryl ether sulfosuccinate | 3.5 |
| Decylglucoside (P.D.: ~1.4) | 5.5 |
| Cocoamidopropyl betaine | 7.0 |
| Cetyl PEG/PPG-10/1 dimethicone | 0.5 |
| Cationic polymer (Polyquaternium-10) | 0.2 |
| Sodium benzoate | 0.6 |
| HC red 3 | 0.1 |
| Basic brown 16 | 0.02 |
| PEG-160 sorbitan triisostearate | 0.5 |
| PEG-18 Glyceryl cocoate/oleate | 0.8 |
| Malic acid | 0.8 |
| Perfume | 0.5 |
| Water | ad 100.0 | pH of the composition is 3.6.

The properties of this shampoo corresponded with those according to previous examples. The color observed on hair after washing and drying is red-brown.

EXAMPLE 6

| | |
|---|---|
| Sodium lauryl ether sulfate | 9.0 (% by wt.) |
| $C_8$—$C_{22}$-Alkyl glucoside (P.D.: ~1.5) | 4.5 |
| Cocoamidopropyl betaine | 2.0 |
| Cationic polymer (Polyquaternium-10) | 0.1 |
| Cationic polymer (Quaternium-80) | 0.1 |
| Sodium benzoate | 0.5 |
| Perfume | 0.5 |
| Panthenol | 0.1 |
| PEG-60-hydrogenated castor oil | 0.5 |
| PEG-18 Glyceryl cocoate/oleate | 2.0 |
| Benzophenone-3 | 0.1 |
| Basic yellow 87 | 0.0011 |
| Basic Orange 31 | 0.0002 |
| Malic acid | 0.75 |
| Water | ad 100.0 |

The pH of the composition is 3.7. The color direction is warm blond.

EXAMPLE 7

| | |
|---|---|
| Sodium lauryl ether sulfate | 8.0 (% by wt.) |
| $C_8$—$C_{22}$-Alkyl glucoside (P.D.: ~1.5) | 4.0 |
| Cocoamidopropyl betaine | 1.0 |
| Cationic polymer (Polyquaternium-10) | 0.1 |
| Sodium benzoate | 0.5 |
| Benzyloxyethanol | 0.5 |
| Perfume | 0.5 |
| PEG-60-hydrogenated castor oil | 0.5 |
| PEG-18 Glyceryl cocoate/oleate | 2.0 |
| Glycol distearate | 0.75 |
| Benzophenone-3 | 0.1 |
| Basic yellow 87 | 0.0025 |
| Basic Orange 31 | 0.0015 |
| Malic acid | 1.0 |
| Water | ad 100.0 |

The pH of the composition is 3.3. The color direction is copper.

EXAMPLE 8

| | |
|---|---|
| Sodium lauryl ether sulfate | 8.0 (% by wt.) |
| $C_8$—$C_{22}$-Alkyl glucoside (P.D.: ~1.5) | 4.0 |
| Cocoamidopropyl betaine | 1.0 |
| Glycol Distearate | 1.0 |
| Cationic polymer (quaternized Guar) | 0.3 |
| Cationic polymer (Quaternium-80) | 0.2 |
| Laureth-4 | 0.4 |
| Sodium benzoate | 0.55 |
| Hydrolyzed Silk | 0.05 |
| Perfume | 0.4 |
| PEG-60-hydrogenated castor oil | 0.5 |
| PEG-18 Glyceryl cocoate/oleate | 2.0 |
| Basic Red 51 | 0.00130 |
| Basic Brown 17 | 0.24475 |
| Basic Blue 99 | 0.03500 |
| HC Red 3 | 0.00225 |
| Malic acid | 0.75 |
| Lactic acid | 0.35 |
| Water | ad 100.0 |

The pH of the composition is 3.3. The color direction is mahogany to brown.

The invention claimed is:

1. Coloring enhancing shampoo composition for hair, comprising at least one surfactant selected from anionic, non-ionic by amphoteric or zwitterionic surfactants, at least one cationic direct dyestuff and at least one hydroxycarboxylic acid and/or dicarboxylic acid and has a pH value less than 4.5, wherein concentration of surfactant is in the range of 1 to 50% by weight calculated to the total composition.

2. Composition according to claim 1, wherein it comprises at least one anionic surfactant and at least one non-ionic surfactant.

3. Composition according to claim 2, wherein it comprises additionally at least one amphoteric surfactant.

4. Composition according to claim 1, wherein it has a pH in the range of 2.5 to 4.0.

5. Composition according to claim 1, wherein it has a pH in the range of 2.9 to 3.8.

6. Composition according to claim 1, wherein concentration of cationic direct dye is in the range of 0.0001 to 2% by weight calculated to the total composition.

7. Composition according to claim 1, wherein concentration of at least one hydroxycarboxylic acid and/or dicarboxylic acid is in the range of 0.1 to 5% by weight calculated to the total composition.

8. Composition according to claim 1, wherein it comprises malic acid and/or lactic acid as hydroxycarboxylic acid.

9. Composition according to claim 1, wherein it comprises hydroxycarboxylic acid at concentration of 0.5 to 5% by weight with the condition that it comprises malic acid at a concentration of not less than 0.5% by weight calculated to total composition.

10. Composition according to claim 1, wherein it comprises only malic acid as a hydroxycarboxylic acid and/or dicarboxylic acid.

11. Composition according to claim 1, wherein it comprises cationic polymers as a conditioner.

12. Composition according to claim 1, wherein it comprises organic solvents at a concentration of less than 5% by weight calculated to total composition.

13. Composition according to claim 1, wherein it is a transparent composition.

14. Composition according to claim 1, wherein it is a non-transparent pearly composition and contains perlizing agents at a concentration of 0.1 to 3% by weight calculated to total composition.

15. Method of use of a composition according to claim 1 for color and shine enhancing of hair.

* * * * *